US007947044B2

(12) United States Patent
Ullrich, Jr. et al.

(10) Patent No.: US 7,947,044 B2
(45) Date of Patent: May 24, 2011

(54) SURGICAL INSTRUMENTS FOR SHAPING SPINAL ENDPLATES

(75) Inventors: Peter F. Ullrich, Jr., Neenah, WI (US); Charanpreet S. Bagga, Phoenixville, PA (US)

(73) Assignee: Orthovita, Inc., Malvern, PA (US)

( * ) Notice: Subject to any disclaimer, the term of this patent is extended or adjusted under 35 U.S.C. 154(b) by 0 days.

(21) Appl. No.: 12/137,760

(22) Filed: Jun. 12, 2008

(65) Prior Publication Data

US 2008/0243128 A1    Oct. 2, 2008

Related U.S. Application Data

(63) Continuation of application No. 10/973,481, filed on Oct. 26, 2004, now abandoned.

(51) Int. Cl.
*A61B 17/00* (2006.01)
(52) U.S. Cl. .......................... 606/79; 606/85; 606/86 R
(58) Field of Classification Search .................. 606/79, 606/80, 84, 85, 86 R, 96
See application file for complete search history.

(56) References Cited

U.S. PATENT DOCUMENTS

| | | | |
|---|---|---|---|
| 5,152,792 A | 10/1992 | Watkins et al. | 606/87 |
| 5,484,437 A | 1/1996 | Michelson | 606/61 |
| 5,505,732 A | 4/1996 | Michelson | 606/61 |
| 5,797,909 A | 8/1998 | Michelson | 606/61 |
| 6,059,790 A * | 5/2000 | Sand et al. | 606/99 |
| 6,063,088 A | 5/2000 | Winslow | 606/61 |
| 6,080,155 A | 6/2000 | Michelson | 606/61 |
| 6,096,038 A | 8/2000 | Michelson | 606/61 |
| 6,159,214 A | 12/2000 | Michelson | 606/80 |
| 6,200,322 B1 | 3/2001 | Branch et al. | 606/96 |
| 6,224,599 B1 * | 5/2001 | Baynham et al. | 606/90 |
| 6,228,022 B1 | 5/2001 | Friesem et al. | 600/204 |
| 6,241,729 B1 | 6/2001 | Estes et al. | 606/61 |
| 6,270,498 B1 | 8/2001 | Michelson | 606/61 |
| 6,283,966 B1 | 9/2001 | Houfburg | 606/61 |
| 6,428,541 B1 | 8/2002 | Boyd et al. | 606/61 |
| 6,436,101 B1 | 8/2002 | Hamada | 606/85 |
| 6,440,139 B2 | 8/2002 | Michelson | 606/80 |
| 6,500,206 B1 | 12/2002 | Bryan | 623/17.16 |
| 6,506,151 B2 | 1/2003 | Estes et al. | 600/226 |
| 6,517,544 B1 * | 2/2003 | Michelson | 606/80 |
| 6,524,318 B1 | 2/2003 | Longhini et al. | 606/86 |
| 6,575,981 B1 | 6/2003 | Boyd et al. | 606/90 |
| 6,582,437 B2 | 6/2003 | Dorchak et al. | 606/90 |
| 7,156,849 B2 | 1/2007 | Dunbar et al. | 606/61 |
| 7,175,633 B2 | 2/2007 | Roth et al. | 606/99 |
| 7,320,688 B2 | 1/2008 | Foley et al. | 606/99 |
| 2002/0022847 A1 | 2/2002 | Ray et al. | 606/96 |
| 2006/0084986 A1 | 4/2006 | Grinberg et al. | 606/61 |

* cited by examiner

Primary Examiner — Nicholas Woodall
(74) Attorney, Agent, or Firm — Stradley Ronon Stevens & Young, LLP

(57) ABSTRACT

The present invention relates to surgical instruments particularly suitable for preparing vertebral endplates during spinal interbody surgical procedures. Methods of using such instruments are also disclosed.

18 Claims, 4 Drawing Sheets

SURGICAL INSTRUMENTS FOR SHAPING SPINAL ENDPLATES

CROSS REFERENCE TO RELATED APPLICATIONS

This application is a continuation of U.S. application Ser. No. 10/973,481, filed Oct. 26, 2004, the entirety of which is incorporated herein.

FIELD OF THE INVENTION

This invention relates to surgical instruments and methods of using such instruments. The instruments are particularly suitable for preparing vertebral endplates during spinal interbody implant procedures.

BACKGROUND OF THE INVENTION

In the simplest terms, the spine is a column made of vertebrae and discs. The vertebrae provide the support and structure of the spine while the spinal discs, located between the vertebrae, act like cushions or "shock absorbers." These discs also contribute to the flexibility and motion of the spinal column. Over time, the discs may become diseased, infected, develop deformities such as tears/cracks, or simply lose structural integrity, for example, bulge or flatten. These impaired discs can affect the anatomical functions of the vertebrae, due to the resultant lack of proper biomechanical support, and are often associated with chronic back pain. Chronic back pain afflicts a large percentage of the world's population and often interferes with one's ability participate in regular daily activities.

Several surgical techniques have been developed to address spinal defects, such as disc degeneration and/or deformity. Spinal fusion has become a recognized surgical procedure for restoring biomechanical and anatomical integrity to the spine. Spinal fusion techniques involve the removal, or partial removal, of at least one intervertebral disc and preparation of the disc space for receiving an implant by shaping the exposed vertebral endplates, an implant is then inserted between the opposing endplates. Vertebral endplates can have complex shapes due to various anatomical and biological factors. For example, a vertebral endplate may be concave in some portions. The vertebral endplates may also have surface irregularities and even bony protuberances, or osteophytes, which can be difficult to remove. These osteophytes, found predominately about the posterior-lateral portions of the endplate, are especially problematic as they can painfully impinge on nearby anatomical structures and reduce the useable implant-seating surface to primarily the medial-anterior portion of the disc space. This reduction in seating area may compromise biomechanical integrity by reducing the area in which to distribute mechanical forces, thus increasing the apparent stress experienced by both the implant and vertebral endplate.

Proper endplate preparation is important to successful spinal fusion surgery procedures. To achieve fusion, it is generally necessary to expose bleeding endplate bone stock. This initiates the biological healing process of the bone and encourages implant integration. The surgeon must also conform or shape the endplate to, at least, approximate the implant geometry thereby ensuring proper seating of the spinal implant in the disc space. One of the many challenges of preparing the endplates is the discrepancy between the shape of the endplates and the implant. While the spinal endplates may have a complex surface topography, the mating surfaces of spinal implants are generally flat. Thus, the surgeon may initially desire to provide the maximum surface area for proper implant seating by simply razing enough endplate bone stock to ensure a relatively flat surface.

In addition to maximizing the surface area available for implant seating, the surgeon should also preserve as much surface vertebral endplate bone as possible by minimizing the amount of bone removed since this subchondral bone is generally much stronger than the underlying cancellous bone. Preservation of the endplate bone stock ensures biomechanical integrity of the endplates and minimizes the risk of implant subsidence. Thus, the surgeon should provide for optimal seating of the implant while still maximizing the amount of available securing endplate bone stock.

The surgeon may rely on a number of instruments during complex spinal surgical procedures. With the advent of spinal fusion surgery and the development of spinal implants, there is an increasing need for complimentary instruments. These complimentary instruments should reduce the "instrument load" on the surgeon while increasing the efficiency and precision of the surgical procedure. These instruments should also compliment the final size and shape of the implant to be used; again increasing the efficiency of the surgical procedure, while decreasing the overall need for multiple instruments. While there are many instruments that may be required for such complex spinal surgical procedures, there is a need in the art for a single instrument suitable for preparing vertebral endplates to properly receive a spinal implant for spinal surgery procedures.

Methods of endplate preparation have traditionally been performed "by-hand" using a variety of instruments. Traditional free-hand instruments such as box chisels, osteotomes, curettes, drills, milling instruments and the like, which aid in shaping the endplate, also aggressively, and sometimes unevenly, remove bone. Even when used by the most skilled surgeons, these traditional free-hand instruments may prove difficult to control in order to achieve uniform and reproducible results during endplate preparation. The surgeon must also avoid damaging nearby anatomical structures, such as the spinal cord or vertebral arteries. These previously known "by-hand" methods and instruments are generally cumbersome, lack precision, and may lead to the removal of excessive amounts of vertebral endplate bone stock.

None of these approaches provide a single multi-purpose surgical instrument, as is now taught, for allowing controlled and precise preparation of vertebral endplates while preserving endplate bone stock. Thus, there is a need in the art for a single spinal surgical instrument which reduces the instrument load and the number of operating steps for a surgeon, improves visualization of the disc space while minimizing exposure of the disc space, and improves surgical safety by increasing the precision of complimentary free-hand instruments while reducing the risk of damage to nearby anatomical structures.

There is a further need in the art for an instrument for the improved preparation of spinal endplates, especially one which can be used to prepare the posterior-lateral regions of the endplates and/or the entire endplate. There is also a need for a single instrument that can be flipped about its longitudinal axis outside of the disc space, and re-inserted to address features of both the left and right posterior-lateral regions of a vertebral endplate. For example, a single multi-purpose instrument capable of preparing both the lateral and contralateral sides of a vertebral endplate. Still further there is a need for a single instrument capable of preparing both the left and right posterior-lateral regions of vertebral endplates and for removing osteophytes.

SUMMARY OF THE INVENTION

The present invention is directed to surgical instruments and methods of using such instruments. The instruments are particularly suitable in spinal surgeries for preparing a vertebral endplate during an anterior approach procedure.

Certain preferred embodiments of the present invention provide for precise and controlled preparation of vertebral endplates using free-hand surgical instruments. Certain preferred embodiments of the present invention also provide for improved safety in addressing features of the vertebral endplate posterior-lateral regions, including the removal of posterior-lateral osteophytes. Still other preferred embodiments allow for improved visualization of the disc space during surgical procedures while minimizing exposure of the operating space.

Certain embodiments of the present invention include a surgical instrument having both a rasp and a guide body. The instrument has a generally D-shaped first portion which is longitudinally offset from, and connected to, a generally rectangular shaped second portion. The first portion serves as a rasp, while the second portion includes an access port that serves as a device guide. As used herein, a device for use in accordance with certain embodiments of the present invention may be, without limitation, any free-hand instruments including a reamer, box chisel, osteotome, curette, drill, milling instrument or the like, which aid in preparing vertebral endplates. The second portion may also include any number of housings or structures capable of guiding a device such as, for example and without limitation, through-holes, access ports, frames, carriages, tracks, etc. Still further, the device may be controllably advanced along the longitudinal axis of the second portion. The second portion may further include a threaded opening for attachment to a threaded holder.

BRIEF DESCRIPTION OF THE DRAWINGS

FIG. 2B further depicts an embodiment having a contact member only on the upper surface, while

DETAILED DESCRIPTION OF ILLUSTRATIVE EMBODIMENTS

Certain presently preferred aspects of the present invention may be used for the preparation of spinal endplates for a variety of interbody implant procedures. These procedures include, but are not limited to, spinal fusion, vertebral body replacement, and artificial disc procedures. Thus, certain embodiments of the present invention are directed to an instrument and method for use in spinal surgery procedures. Certain embodiments of the surgical instrument are particularly suitable for procedures in which an implant is placed between adjacent vertebrae, such as in spinal fusion procedures, or those which use an implant to replace all or part of one or more vertebral bodies such as during vertebral body replacement procedures. For either procedure, stability of the implant is a major concern, thus implant loosening and/or motion should be avoided as either condition may impair implant performance, result in anatomical damage, present substantial pain to the patient, and may result in implant expulsion from the disc space. As such, proper preparation of the disc space and, particularly, the spinal endplates is critical.

Figure 1A:
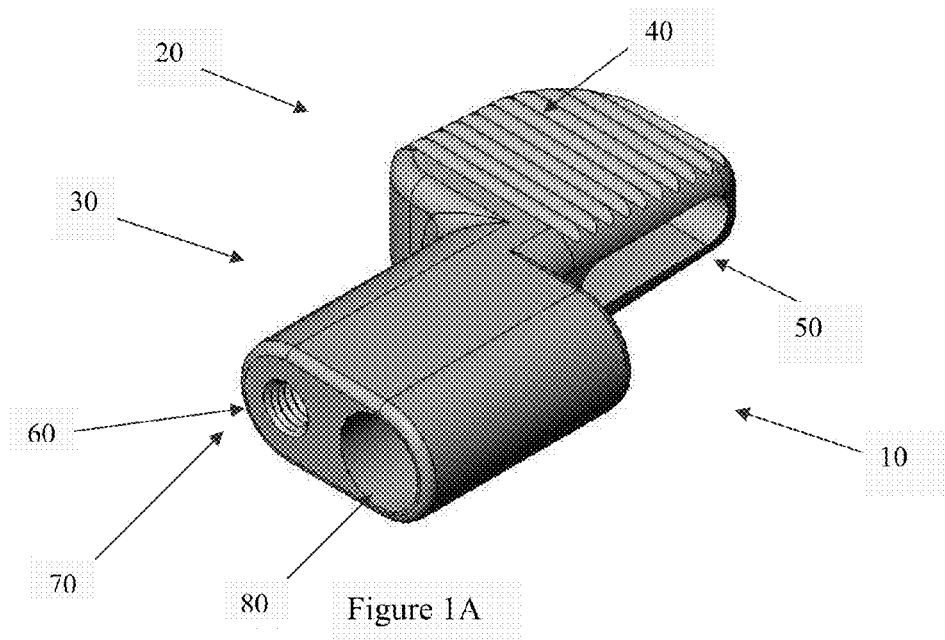
FIG. 1A shows a perspective view of an embodiment of one surgical instrument of the invention (10) having a generally D-shaped first portion (20) and a second portion (30).
Figure 1B:
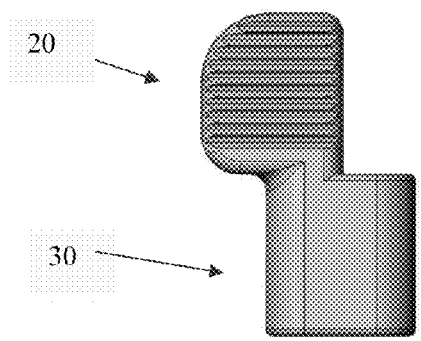
FIG. 1B further depicts a top view of the same embodiment. Lastly.
Figure 1C:
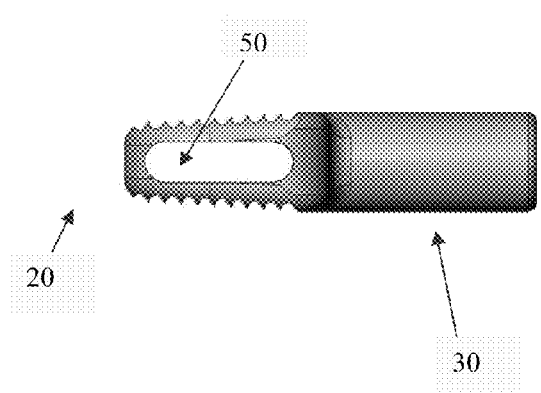
FIG. 1C depicts a side view of the embodiment showing a transverse aperture (50) of the D-shaped portion (20).
Figure 2A:
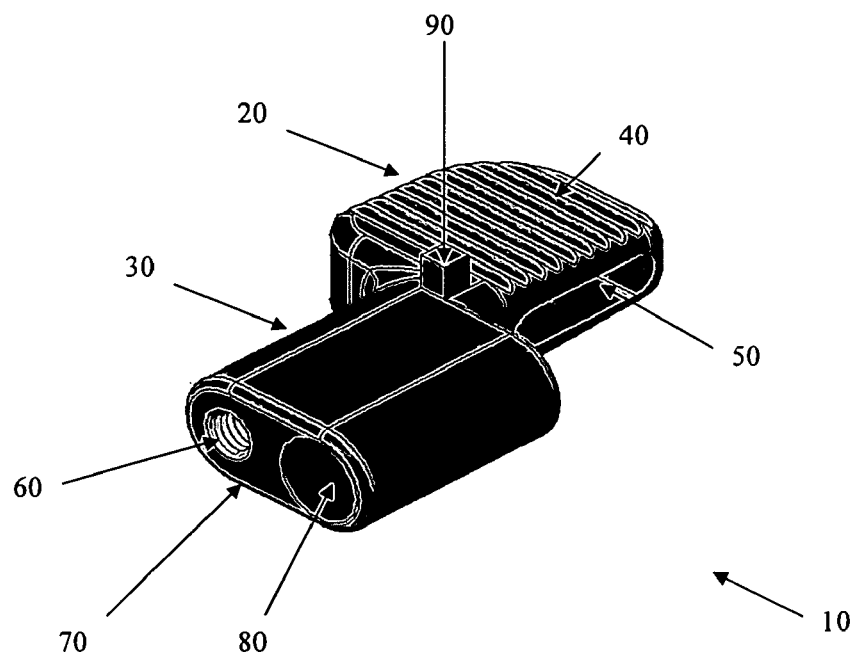
FIG. 2A is a perspective view of an embodiment of the surgical instrument (10) having a contact member (90).
Figure 2B:
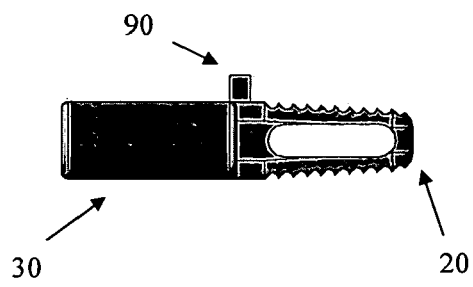
Figure 2C:
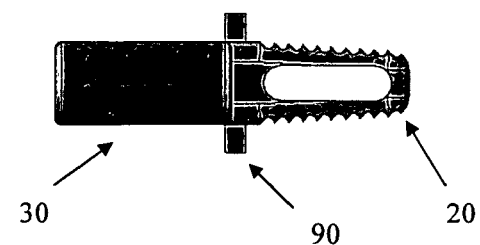
FIG. 2C depicts contact members (90) on both the upper and lower surfaces.
Figures 3A, 3B:
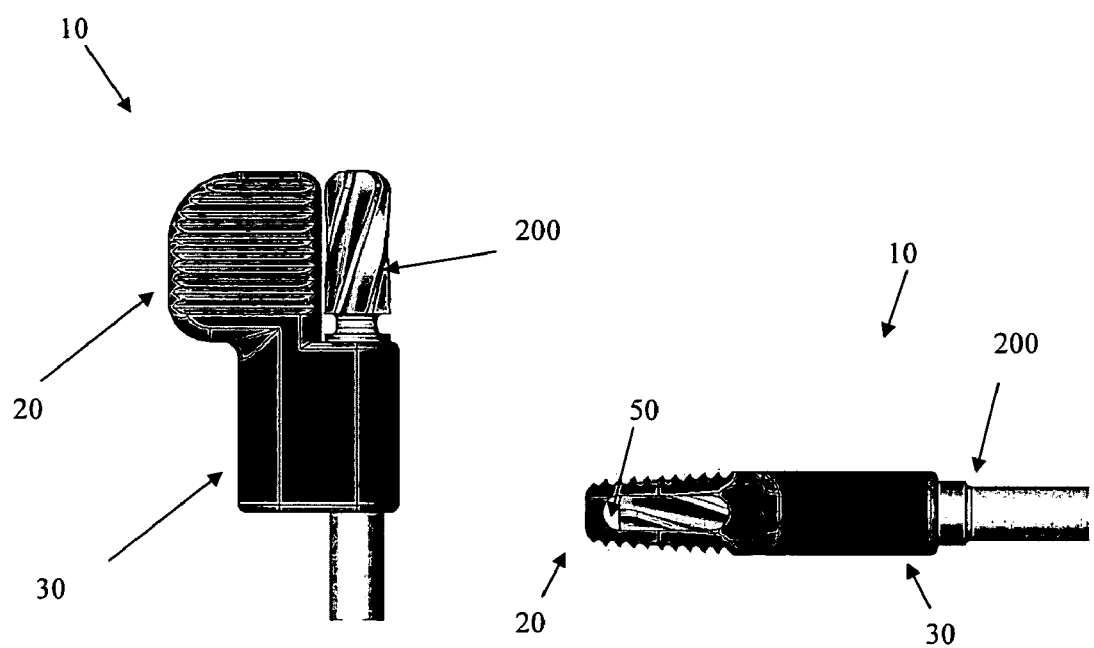
FIG. 3A depicts a top view of an embodiment of the surgical instrument (10) configured to accept a reamer (200) though device guide (80).
FIG. 3B depicts a side view of the surgical instrument (10) showing visualization of the reamer through the transverse aperture (50).
Figure 4:
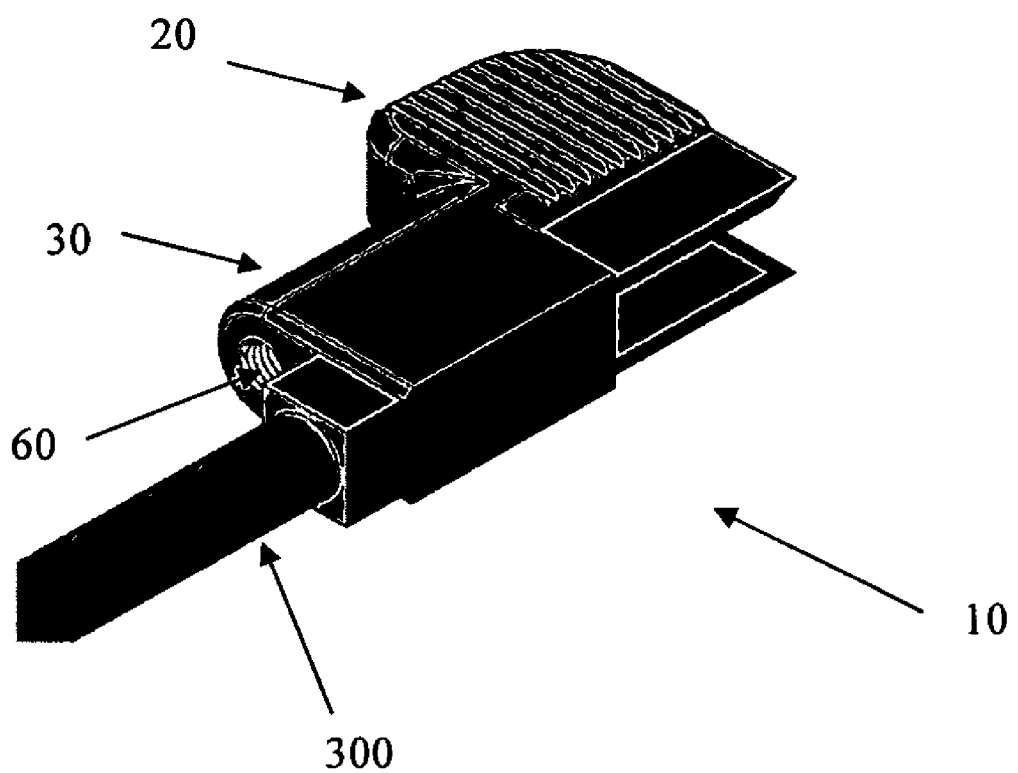
FIG. 4 illustrates a perspective view of an embodiment of the surgical instrument (10) configured to accept a box chisel (300).

In accordance with certain embodiments of the present invention, a surgical instrument is provided comprising both a rasp and a device guide. As shown in FIG. 1, the instrument (10) includes a generally D-shaped first portion (20) which is longitudinally offset, and connected, to a generally rectangular shaped second portion (30). The posterior-lateral-most aspect of the first portion (20) is rounded such that its contour matches the posterior-lateral aspects of the interbody implant for good conformity. Both the top and bottom surfaces of the first portion include rasp (40) for endplate preparation. Alternatively, first portion (20) may have a rasp (40) on either the top or bottom surfaces. Rasp (40) may cover any degree of the top and/or bottom surfaces, but preferably cover the entire top and bottom surface of the first portion. The first portion (20) also includes an aperture (50) that extends the entire transverse length of the first portion (20), thus the first portion may be predominantly hollow. Alternatively, first portion 20 may include a plurality of apertures (50) having uniform or varied size/shape. These apertures (50) aid in the fluoroscopic visualization of a device, such as reamer (200), during a surgical procedure as either an embodiment of the surgical instrument of the present invention or a reamer is advanced into the disc space. The second portion (30) includes a threaded opening (60) on the most proximal end surface, or front face, (70) for attachment to a threaded holder (not shown). The second portion (30) also includes an access port that serves as a device guide (80) adjacent the threaded opening (60). Device guide (80) is particularly useful for controlling the trajectory of free-hand devices, thus increasing the precision of the surgical procedure while also providing for controlled removal of bone in the posterior-lateral regions. First portion (20) may be substantially planar or substantially cylindrical. First portion (20) may also act as a stabilizing element in reducing vibration, and other unwanted movement, while improving free-hand instrument balance and precision. First portion (20), including rasp portion (40), may further serve as a standard rasp for initial preparation and roughening of the vertebral endplate surface with minimal bone removal. The surgeon may therefore choose to skip an initial rasping step using a standard free-hand rasp, and may instead use certain embodiments of the present invention for rasping as well as targeted bone removal. The first portion and/or second portion may also have at least one graded marking or measurement, to gauge the depth of penetration into the disc space.

Certain embodiments of the present invention may also include at least one raised shoulder or contact member (90). The contact members may be any variety of sizes or shapes, so designed to abut at least one adjacent vertebral body. The contact members may also be slidably and/or rotatably connected to second portion (40). Still further, contact member (90) may be extendable to abut a plurality of adjacent vertebrae, as needed. Contact member (90) may be particularly useful in preventing or minimizing damage to nearby anatomical structures.

Preferred embodiments of the present invention are particularly suited for shaping the lateral aspects of the posterior portion of the endplate. The instruments of the present invention can be used with a variety of implants. In particular, those implants having a generally annular shape with rounded corners, for example elliptical or "D" shaped, may be used in accordance with the present invention. In still other preferred embodiments of the present invention device guide (80) may be used with a reamer. In use, a reamer (200) is inserted through the device guide (80) and used to precisely shape the lateral aspects of the posterior portion of the endplate to match the corresponding geometry of the implant. The reamer also aids in the removal of posterior osteophytes and may be provided with a depth control feature such as collet or shoulder to prevent the reamer from breaching the disc space and damaging nearby anatomical structures. For the remainder of the endplate preparation, the rasp portion (40) of the instrument (10) is used. Thus, the present invention allows easy and precise reaming of the lateral corners of the posterior endplate, while at the same time provides a rasp for preparing the remainder of the endplate. The instrument can be flipped 180° about the longitudinal axis of device guide (80) (an imaginary line which runs orthogonal to the front face (70) of the instrument (10) to the distal end of the instrument and would run parallel to the longitudinal centerline of an inserted reamer device). In this manner, the instrument can first be used to prepare the left side of the endplate, removed from the disc space, rotated 180°, and re-inserted to the disc space to prepare the right side of the endplate. This "flipping" action is particularly convenient in cases where there are posterior-lateral osteophytes which require removal prior to preparing the disc space. Thus, certain preferred embodiments of the present invention can be flipped to remove osteophytes on both sides of the endplate, then used to properly ream and prepare the disc space.

In certain embodiments of the present invention, the second portion (30) may also include a threaded opening (60) on the most proximal end surface, or front face, (70) for attachment to a threaded holder (not shown). Still further, second portion (30) may be removably attached to a holder by a variety of engagement structures including, but not limited to, interlocking components or snug-fit mating components. In other embodiments, the present invention is integral with a holder (not shown). And yet in other embodiments, the first portion (20), second portion (30), and holder are all modular components that are assembled during surgery.

In still other embodiments of the present invention, second portion may also include any number of housings or structures capable of guiding a device such as, for example and without limitation, through-holes, access ports, frames, carriages, tracks, etc. Embodiments of device guide (80) may be any number of shapes including, circular, rectangular, irregular, or custom shaped to particular device. Still further, the device may be controllably advanced along the longitudinal axis of the second portion. The second portion may further have any number of mechanisms or structures which facilitate controllable device advancement therefrom. For example, and without limitation, the second portion (30) may contain a threaded access port (80) to accept a threaded reamer; a track, carriage or frame that may be controllably extended from the second portion; an access port (80) having an internal ratchet or other stop-motion mechanism operatively engaged with a reamer; and/or a telescoping access port (80). Thus, second portion (30) may provide for controlled reamer (200) advancement, and controlled reaming depth, into the disc space. Controlled depth of reaming may be particularly useful in preventing, minimizing or even eliminating damage to the surrounding anatomical structures. An alternate embodiment of the present instrument may be configured for use with a free-hand box chisel, or similar instrument. In this manner, access port (80) of second portion (30) serves as a device guide for improved safety, uniformity, and precision of a chisel device.

Embodiments of the present surgical instrument are preferably made of a durable material such as stainless steel, stainless steel alloy, titanium, or titanium alloy, but can also be made of other durable materials such as, but not limited to, polymeric, ceramic or composite materials. Durable materials may also consist of any number of pure metals and/or metal alloys. Certain embodiments of the present invention may also include more than one material. For example, the first portion may be made of a metal alloy and the second portion may be made of a ceramic material.

Certain preferred embodiments of the present invention may include a rasp portion (40) of various sizes. In certain embodiments of the invention, modular rasp portion (40) may be provided in varying sizes, shapes, and/or degrees of coarseness, which may be connected to the remaining modular components during surgery. For example, first portions (20) of various size, etc. may be removably connectable to a single base second portion (30), or alternatively may be assembled to various second portions (30). In yet still another embodiment, there may be multiples, or series, of instrument (10) each having a rasp portion (40) of various sizes, or shapes and/or degrees of coarseness, which are made available during surgery. Still further, rasp portion (40) may act as a spacer to maintain a desired intradiscal height while the lateral aspects of the endplates are prepared to a desired shape using a reamer or other suitable tool. Thus, the entire spinal endplate final geometry can be conveniently prepared to match a desired implant geometry for optimal seating of the implant in the disc space.

Different sizes of rasp portion (40) may cover various percentages of the available medial-lateral disc space. For example, one embodiment of rasp portion (40) may cover the entire medial-lateral width of the disc space. While other embodiments of rasp portion (40) may cover 50%, or more, of the medial-lateral width of the disc space with the remainder of the instrument serving as a guide for a reamer designed particularly for preparation of the spinal endplate, including removal of posterior-lateral osteophytes in the disc space. In yet another embodiment of the present invention, the entire width of the instrument is equivalent to the entire width of the implant to be inserted.

EXAMPLE

A certain embodiment of the present invention was used to prepare spinal endplates to receive a vertebral body replacement. In this surgical procedure, the spine was first exposed via an anterior approach and the center of the target disc was identified. The anterior annulus was then removed and a complete discectomy was performed. Residual cartilage was removed from the spinal endplates to expose bleeding bone. The resultant disc space was distracted by impacting sequentially larger heights of distractors/trial spacers into the disc space, until a tight feel was obtained.

Spinal endplate preparation started with a standard general rasp which was impacted into the disc space for initial coarse rasping and then removed. A size-specific rasp-reamer guide instrument (10) of the present invention was then used to remove strong osteophytes in the posterior-lateral region of the spinal endplate. The size specific rasp-reamer guide instrument (10) was impacted into the disc space via the end face of an optional instrument holder connected via opening (60).

A size-specific reamer (200) was advanced through the opening (80) of size specific rasp-reamer guide instrument (10), under fluoroscopic guidance, to remove posterior osteophytes on one side. A size-specific reamer (200) and rasp-reamer guide instrument (10) were then removed from the disc space. The rasp-reamer guide instrument (10) was then flipped about 180° about the longitudinal axis of reamer guide (80), and the previously discussed steps were repeated for the contra-lateral side of the spinal endplate.

After adequately preparing the endplates, the appropriately sized implant was selected, packed with graft material and placed in the prepared disc space.

Those skilled in the art will appreciate that numerous changes and modifications can be made to the many embodiments of the invention and that such changes and modifications can be made without departing from the spirit of the invention. It is therefore intended that the appended claims cover all such equivalent variations as falling within the true spirit and scope of the invention.

What is claimed:

1. A surgical instrument for use in spinal surgery comprising a longitudinal axis and a first portion and a second portion; wherein said first portion and second portion are longitudinally offset from each other and a section of the proximal end the first portion is connected to a section of the distal end of the second portion;
    said first portion is generally D-shaped in a transverse cross-section and further comprises a top and bottom surface having rasp teeth;
    said first portion further including at least one aperture that extends the entire transverse length of said first portion;
    said second portion has a generally rectangular shaped body and comprises an access portion extending parallel to the longitudinal axis of the instrument and extending through the body of the second portion;
    said second portion is adapted for removable attachment to a holder;
    and wherein the instrument has a transverse axis orthogonal to the longitudinal axis and the first and second portions have a substantially equivalent width along the transverse axis of the instrument.

2. The surgical instrument of claim 1, wherein at least one of said first and second portion further comprises at least one contact member.

3. The surgical instrument of claim 2, wherein said at least one contact member is extendable from at least one of said first and second portion.

4. The surgical instrument of claim 1, wherein said instrument is comprised of a durable material.

5. The surgical instrument of claim 4, wherein the durable material is at least one of a pure metal and metal alloy.

6. The surgical instrument of claim 1, wherein the access port is a device guide.

7. The surgical instrument of claim 6, wherein the device guide is adapted to control a free-hand device for shaping vertebral endplates selected from the group consisting of a reamer, box chisel, osteotome, curette, drill, and milling instrument.

8. The surgical instrument of claim 1, wherein the adaptation of the second portion for removable attachment to a holder is a threaded opening on the proximal end of the second portion.

9. The surgical instrument of claim 8, wherein the threaded opening is parallel to the longitudinal axis of the instrument.

10. The surgical instrument of claim 1, wherein the access port is cylindrical.

11. A surgical instrument for use in spinal surgery comprising a longitudinal axis and a first portion and a second portion; wherein said first portion and second portion are longitudinally offset from each other and a section of the proximal end of the first portion is connected to a section of the distal end of the second portion;
    said first portion is generally D-shaped in a transverse cross-section and further comprises a top and bottom surface having rasp teeth;
    said first portion further including at least one aperture that extends the entire transverse length of said first portion;
    said second portion have (a) a generally rectangular shaped body, (b) a device guide extending parallel to the longitudinal axis of the instrument and extending through the body of the second portion, and (c) an opening extending parallel both to the longitudinal axis of the instrument and to the adjacent device guide, extending at least partway through the body of the second portion, and being adapted for removable attachment to a holder;
    and wherein the instrument has a transverse axis orthogonal to the longitudinal axis and the first and second portions have a substantially equivalent width along the transverse axis of the instrument.

12. The surgical instrument of claim 11, wherein the device guide is adapted to control a free-hand device for shaping vertebral endplates selected from the group consisting of a reamer, box chisel, osteotome, curette, drill, and milling instrument.

13. The surgical instrument of claim 11, wherein the opening of the second portion is a threaded opening.

14. The surgical instrument of claim 11, wherein the device guide is cylindrical.

15. The surgical instrument of claim 11, wherein at least one of the first and second portion further comprises at least one contact member.

16. The surgical instrument of claim 11, wherein the instrument is comprised of a durable material selected from at least one of a pure metal and a metal alloy.

17. A surgical instrument for use in spinal surgery comprising a longitudinal axis and a first portion and a second portion; wherein said first portion and second portion are longitudinally offset from each other and a section of the proximal end of the first portion is connected to a section of the distal end of the second portion;
    said first portion is generally D-shaped in transverse cross-section and further comprises a top and bottom surface having rasp teeth;
    said first portion further including at least one aperture that extends the entire transverse length of said first portion;
    said second portion has (a) a generally rectangular shaped body, (b) a cylindrical device guide extending parallel to the longitudinal axis of the instrument, extending entirely through the body of the second portion, and being adapted to control a free-hand device for shaping vertebral endplates selected from the group consisting of a reamer, box chisel, osteotome, curette, drill, and milling instrument, and (c) an opening extending parallel both to the longitudinal axis of the instrument and to the adjacent device guide, extending at least part-way through the body of the second portion, and being adapted for removable attachment to a holder, wherein the instrument is made of a durable material and has a transverse axis orthogonal to the longitudinal axis, and the first and second portions have a substantially equivalent width along the transverse axis of the instrument.

18. The surgical instrument of claim 17, wherein at least one of the first and second portion further comprises at least one contact member.

* * * * *